(12) United States Patent
Ritter

(10) Patent No.: US 7,029,702 B2
(45) Date of Patent: Apr. 18, 2006

(54) METHOD FOR INCREASING LACTOSE TOLERANCE IN MAMMALS EXHIBITING LACTOSE INTOLERANCE

(75) Inventor: Andrew J. Ritter, Los Angeles, CA (US)

(73) Assignee: Ritter Natural Sciences LLC, Los Angeles, CA (US)

( * ) Notice: Subject to any disclaimer, the term of this patent is extended or adjusted under 35 U.S.C. 154(b) by 0 days.

(21) Appl. No.: 09/346,479

(22) Filed: Jul. 1, 1999

(65) Prior Publication Data

US 2002/0034496 A1    Mar. 21, 2002

Related U.S. Application Data

(60) Provisional application No. 60/091,971, filed on Jul. 7, 1998.

(51) Int. Cl.
*A61K 35/20* (2006.01)

(52) U.S. Cl. .................. 424/535; 424/93.4; 424/93.44; 424/93.45; 426/43

(58) Field of Classification Search ............... 424/93.4, 424/93.44, 93.45, 535; 426/43
See application file for complete search history.

(56) References Cited

U.S. PATENT DOCUMENTS 5,952,021 A * 9/1999 Santus

OTHER PUBLICATIONS

Kim et al. Journal of Dairy Science, vol. 66, pp. 959-966, 1983.*

Onwulata et al. American Journal of Clinical Nutrition, vol. 49, pp. 1233-1237, 1989.*

Martini et al. Am. J. Clin. Nutr. (1991), vol. 53, pp. 1253-1258.*

National Digestive Diseases, "Lactose Intolerance",http://www.niddk.gov/health/digest/pubs/lactose/lactose.htm, 1999.

DFO-Nutrition Services: Spotlight For September, 1995 "Lactose Intolerance: Common Concerns", http://www.milk.org/spotsept.htm.

* cited by examiner

*Primary Examiner*—Susan D. Coe
(74) *Attorney, Agent, or Firm*—Wilson Sonsini Goodrich & Rosati

(57) ABSTRACT

The method for increasing lactose tolerance in subjects exhibiting lactose intolerance symptoms implements a protocol where the subjects ingest a gradually increasing amount of lactose containing product over a six week period. At various points during the six week period the subject ingests the lactose containing product once a day and then twice a day. The lactose containing product can be in liquid form, such as for example, milk, and is preferably in a powder form which is taken either by ingesting capsules having the lactose powder or in a granular form mixed with water or other non-lactose containing liquid. At the end of the six week period, the subject's tolerance for lactose containing products is substantially increased, with the potential of eliminating the subject's lactose intolerant behavior indefinitely.

7 Claims, No Drawings

METHOD FOR INCREASING LACTOSE TOLERANCE IN MAMMALS EXHIBITING LACTOSE INTOLERANCE

RELATED APPLICATION INFORMATION

This application claims priority from U.S. Provisional Patent Application Ser. No. 60/091,971 filed on Jul. 7, 1998.

FIELD OF THE INVENTION

The present invention relates to a method for increasing lactose tolerance in individuals or mammals who exhibit lactose intolerant symptoms.

BACKGROUND OF THE INVENTION

Lactose Intolerance, or otherwise referred to as lactose maldigestion, is the inability to digest a significant amount of lactose, derived from a deficiency of the lactase enzyme in the small intestines. Lactose is the natural sugar in milk and milk products of all mammals. Lactase is the enzyme which splits the milk sugar lactose into its components (i.e., glucose and galactose), and also breaks down the milk sugar into smaller forms that can be processed into the bloodstream. The lactase enzyme is necessary for mammals to digest lactose.

There is an important distinction between lactose intolerance and milk allergies. Lactose intolerance is the inability of the body to digest lactose containing products due to a deficiency in the lactase enzyme. A milk allergy, however, is a sensitivity to the protein in milk, which involves the immune system and does not relate to a deficiency of the lactase enzyme. In humans, a milk allergy is usually experienced only by infants.

Generally, humans develop lactose intolerance from a primary or secondary cause. The primary cause is an onset loss of lactase that is a permanent condition. This occurs at a variable period after the weaning period. The primary cause is also genetically determined. The secondary cause is generally a temporary condition that occurs as a result of another disease or event that damages the lining of the small intestine where lactase is active. This is usually caused by an acute diarrheal disease, parasitic infection, Crohn's disease, celiac disease, gastrointestinal surgery, or the intake of certain medications.

In addition to the primary and secondary causes, certain human ethnic and racial populations have more of a predisposition for lactose intolerance. In these populations, social and cultural habits and attitudes influence lactose intolerance. Lactose activity can also decrease with age in certain ethnic and racial populations, including those populations which have origins in Europe, the African plains, and the Siberian Steppes. Humans who are most likely to have or develop lactose intolerance include those of Asian, Middle Eastern, North American, African, and Latin American descent.

According to several sources, there are 30 to 50 million people in the world who are lactose intolerant. In the 1960's and 1970's, it was reported that 70% of the adults in the world had lactose intolerance. In 1995, is was reported that 75% of the adults in the world and 25% of the adults in the U.S. were categorized as being lactose intolerant. In 1994, it was reported that 75% of African Americans and Native Americans and 90% of Asian Americans had lactose intolerance. It has also been reported that 30% of adults who are mostly North Western and North American descendants of the Europeans, have adapted to high lactase activity into adulthood. Research concludes that this adaptation is genetically controlled, permanent and related to a long tradition of milk and milk products consumption in these regions of the world.

Lactose intolerance can be tested either indirectly or directly. There are three main ways to test by the indirect method: a hydrogen breath test, a stool acidity test, or a blood glucose test. In the hydrogen breath test, the breath is measured to determine the amount of hydrogen produced after consuming a measured amount of lactose, typically 15 g. The lactose is consumed by drinking a lactose mixture, and the subject exhales into a vacuum-sealed collection tube at three one hour time intervals. A high level of hydrogen in the breath indicates an improper digestion of lactose. In a stool test, the stool is tested to determine the amount of acid. In a blood glucose test, the blood is tested to determine the amount of glucose (sugar) content after administering a predetermined amount of lactose-containing product to the subject. The direct method measures lactose activity in a mucosal biopsy specimen.

If an individual suspects that he has lactose intolerance, it is potentially harmful for him to restrict his diet since it may result in a nutrition shortage or a failure to detect a more serious disease. Milk and other dairy products are major sources for nutrition in the basic American diet. The primary nutrients in milk are protein, calcium, riboflavin, vitamin A, and vitamin D. Calcium is an important part of the recommended daily allowances of vitamins and minerals and any deficiency therein can lead to osteoporosis.

When an individual has an allergic reaction to milk, there are several different resulting symptoms depending on the age of the individual. For young adults and adults, symptoms include bloating, nausea, cramps, and diarrhea, while the symptoms in infants are diarrhea, dehydration, malnutrition, and potentially death. Some of the symptoms vary based on the level of tolerance the person has, the amount and type of lactose consumed, or the remainder of the person's diet.

Lactose is not digested when the amount of lactose consumed exceeds the lactase enzyme capacity of the small intestine. Instead, excess undigested lactose passes through the small intestines into the large intestine where it is fermented by a bacteria called colinic flora. The fermentation of the lactose in the large intestine produces hydrogen and methane which can lead to bloating, gas, and diarrhea. These symptoms are caused by a very low activity of lactase in the intestines.

The use of lactase tablets which are generally available, help lactose intolerant people digest milk and milk products. Each lactase tablet typically hydrolyzes up to 99% of the ingested lactose within 24 hours, and is designed to be ingested with the lactose containing food.

Young children who have lactose intolerance are very rare. The amount of lactase enzyme a body produces generally reaches a maximum immediately after birth and then decreases in the majority of people after their body adjusts during the ages of 3–15. A stool test is used to test lactose intolerance in young children. For young children, the breath test is not as accurate because they usually have a tendency to get dehydrated which can cause diarrhea.

The reasons for an onset of lactose intolerance are generally unknown. However, there is a general belief that by consuming small amounts of lactose frequently over a period of time, lactose intolerance can be improved. Whole milk and chocolate milk appear to be tolerated better than low fat milk because the fat content of whole milk and chocolate milk slows the rate of gastric emptying. Many lactose intolerant people can have at least 8 oz of milk. Also, many lactose intolerant people can have hard cheeses because during manufacturing most of the lactose is removed with the whey. During the aging of the cheeses, the remaining lactose is converted to lactic acid and other products. As a result, most aged cheeses have little to no lactose. Some of such firm cheeses include cheddar, Swiss and mozzarella. Another product that lactose intolerant people can tolerate is yogurt, with live culture bacteria in it. Having yogurt with a non-fermented dairy product can improve lactose digestion.

People typically have different symptoms of lactose intolerance. Lactose intolerance may also be psychologically induced. There are also many different variations of lactose intolerance depending on the individual. For example, some individuals cannot have cheese, melted cheese, plain milk, or warm dairy containing products like milk in coffee, while others cannot have any dairy products at all. Also, most lactose intolerant people are limited as to the amount of special "lactose free" foods they can eat that have been manufactured by specific companies. Some examples of these "lactose free" foods are: Mocha Mix ice cream, Tofutti ice cream and ice cream sandwiches, LACTAID® brand milk, Formagg cheese, Tofutti "Better than Cream Cheese", margarine, and live cultured yogurt. The only problem with all these products is that they are not readily available everywhere.

SUMMARY OF THE INVENTION

The present invention provides a method for increasing the lactose tolerance of mammals exhibiting lactose intolerance symptoms. In accordance with the invention, a six-week protocol is employed during which a subject ingests gradually increasing amounts of a lactose-containing product. On the first and second days of the protocol, the subject also ingests a predetermined amount of a live culture bacteria containing compound, such as yogurt. Toward the end of the six-week period, the subject starts ingesting other lactose-containing products while continuing to ingest the predetermined amount of lactose containing product. By the conclusion of the six-week protocol, the subject's tolerance for lactose-containing products is significantly increased, and in some cases, the subject no longer experiences any lactose intolerance or the symptoms associated therewith.

In accordance with a preferred embodiment of the invention, the lactose-containing product is administered to the subject is in the form of a lactose powder. The lactose powder can be provided within an ingestable capsule or in granular form which is measured out and added to the subject meal or drink.

The various features of novelty which characterize the invention are pointed out with particularity in the claims annexed to and forming a part of the disclosure.

DETAILED DESCRIPTION OF PREFERRED EMBODIMENTS

According to a first embodiment of the invention, a predetermined fist dose of a liquid form of a lactose-containing product, such as, for example milk, is administered to the subject once each day in gradually increasing amounts during the course of a six-week period. On the first and second days, a predetermined amount of a substance containing live cultured bacteria, such as yogurt, is administered to the subject with the dose of lactose-containing product. Subsequently, during the six-week period, a second dose of the liquid form of lactose, in addition to the first dose, is administered to the subject at a second time during each day.

An example of this dosing regimen is shown below in Table 1. On the first day, the subject ingests 8 ounces of live culture bacteria yogurt with 1 tablespoon of milk with dinner. On day 2, the amount of yogurt ingested is reduced to 4 ounces and the amount of milk administered remains the same. On day 3, administration of the yogurt is ceased, and the milk dose remains at one tablespoon. During days 4 through 18, the amount of milk ingested with dinner is increased by one tablespoon each day until 16 tablespoons are reached on day 18. On day 19, a second dose, 1 tablespoon, of milk is ingested in the morning with breakfast and 16 tablespoons of milk are ingested with dinner. From day 16 until day 34, the subject continues to ingest 16 tablespoons of milk with dinner. The morning dose is increased daily at a rate of 1 tablespoon per day so that by day 34 the subject ingests 16 tablespoons of milk with breakfast and 16 tablespoons with dinner. On day 35, the subject discontinues ingesting the lactose containing product in tablespoon doses and begins ingesting milk, starting with 9 ounces in the morning and 9 ounces in the evening with the meals. The amount of milk is increased an ounce each day so that by day 38, the subject ingests 12 ounces of milk with both breakfast and dinner. On day 39, the subject discontinues the milk intake and instead ingests 1 ounce of cheese. The amount of cheese is increased to 2 ounces on day 40. By day 41, the subject's lactose intolerance has been completely eliminated, and the subject is free to eat any dairy product of his choice.

TABLE 1

| Week | Day | PM-Dosage | AM-Dosage |
|---|---|---|---|
| 1 | 1 | 1 tbs + 8 oz yogurt | |
| 1 | 2 | 1 tbs + 4 oz yogurt | |
| 1 | 3 | 1 tbs | |
| 1 | 4 | 2 tbs | |
| 1 | 5 | 3 tbs | |
| 1 | 6 | 4 tbs | |
| 1 | 7 | 5 tbs | |
| 2 | 8 | 6 tbs | |
| 2 | 9 | 7 tbs | |
| 2 | 10 | 8 tbs | |
| 2 | 11 | 9 tbs | |
| 2 | 12 | 10 tbs | |
| 2 | 13 | 11 tbs | |
| 2 | 14 | 12 tbs | |
| 3 | 15 | 13 tbs | |
| 3 | 16 | 14 tbs | |
| 3 | 17 | 15 tbs | |
| 3 | 18 | 16 tbs | |
| 3 | 19 | 16 tbs | 1 tbs |
| 3 | 20 | 16 tbs | 2 tbs |
| 3 | 21 | 16 tbs | 3 tbs |
| 4 | 22 | 16 tbs | 4 tbs |
| 4 | 23 | 16 tbs | 5 tbs |
| 4 | 24 | 16 tbs | 6 tbs |
| 4 | 25 | 16 tbs | 7 tbs |
| 4 | 26 | 16 tbs | 8 tbs |
| 4 | 27 | 16 tbs | 9 tbs |
| 4 | 28 | 16 tbs | 10 tbs |
| 5 | 29 | 16 tbs | 11 tbs |
| 5 | 30 | 16 tbs | 12 tbs |
| 5 | 31 | 16 tbs | 13 tbs |
| 5 | 32 | 16 tbs | 14 tbs |
| 5 | 33 | 16 tbs | 15 tbs |
| 5 | 34 | 16 tbs | 16 tbs |
| 5 | 35 | 9 oz milk | 9 oz milk |

TABLE 1-continued

| Week | Day | PM-Dosage | AM-Dosage |
|------|-----|-----------|-----------|
| 6 | 36 | 10 oz milk | 10 oz milk |
| 6 | 37 | 11 oz milk | 11 oz milk |
| 6 | 38 | 12 oz milk | 12 oz milk |
| 6 | 39 | Cheese 2 oz | |
| 6 | 40 | Cheese 2 oz | |
| 6 | 41 | lactose tolerance achieved | |
| 6 | 42 | | |

Table 1 shows exemplary six-week protocol however, the actual days on which the doses are changed and the quantity of the doses can be modified according to the subject and his specific reactions without departing from the scope of the invention. For example, the subject may be capable of ingesting more than 5 tablespoons of milk by day 7, and could therefore increase it to 6 tablespoons on day 7, and so on. Alternatively, the subject may find that the transition from 5 tablespoons on day 7 (which he is capable of ingesting without any adverse effect) to 6 tablespoons on day 8 may result in an adverse effect. As such, the subject may revert back to the 5 tablespoon dose and continue that dose for a longer period than originally prescribed (e.g., 2 or more days) before increasing the dosage again. The same variable modification to the protocol applies to the lactose powder protocol described below with reference to Table 2.

In another embodiment of the present invention, the lactose containing product administered to the subject is a pure powder lactose that is contained in an ingestable capsule or an equivalent amount in a loose granular form mixed with water or other non-lactose containing product. An example of the powder lactose regimen is shown in Table 2. In Table 2, the designation "s" refers to a 1 zero sized capsule filled with 0.8 grams of pure powder lactose (which is equivalent to 1 tablespoon of milk), and "m" refers to a double sized zero capsule filled with 1.6 grams of pure lactose powder. The amount of lactose ingested in any period in accordance with the regimen shown in Table 2 is identical to that of the regimen shown in Table 1 except that the form of the lactose is different.

TABLE 2

| Week | Day | PM-Dosage | AM-Dosage |
|------|-----|-----------|-----------|
| 1 | 1 | s + 8 oz yogurt | |
| 1 | 2 | s + 4 oz yogurt | |
| 1 | 3 | s | |
| 1 | 4 | m | |
| 1 | 5 | m + s | |
| 1 | 6 | 2 m | |
| 1 | 7 | 2 m + s | |
| 2 | 8 | 3 m | |
| 2 | 9 | 3 m + s | |
| 2 | 10 | 4 m | |
| 2 | 11 | 4 m + s | |
| 2 | 12 | 5 m | |
| 2 | 13 | 5 m + s | |
| 2 | 14 | 6 m | |
| 3 | 15 | 6 m + s | |
| 3 | 16 | 7 m | |
| 3 | 17 | 7 m + s | |
| 3 | 18 | 8 m | |
| 3 | 19 | 8 m | s |
| 3 | 20 | 8 m | m |
| 3 | 21 | 8 m | m + s |

TABLE 2-continued

| Week | Day | PM-Dosage | AM-Dosage |
|------|-----|-----------|-----------|
| 4 | 22 | 8 m | 2 m |
| 4 | 23 | 8 m | 2 m + s |
| 4 | 24 | 8 m | 3 m |
| 4 | 25 | 8 m | 3 m + s |
| 4 | 26 | 8 m | 4 m |
| 4 | 27 | 8 m | 4 m + s |
| 4 | 28 | 8 m | 5 m |
| 5 | 29 | 8 m | 5 m + s |
| 5 | 30 | 8 m | 6 m |
| 5 | 31 | 8 m | 6 m + s |
| 5 | 32 | 8 m | 7 m |
| 5 | 33 | 8 m | 7 m + s |
| 5 | 34 | 8 m | 8 m |
| 5 | 35 | 9 oz milk | 9 oz milk |
| 6 | 36 | 10 oz milk | 10 oz milk |
| 6 | 37 | 11 oz milk | 11 oz milk |
| 6 | 38 | 12 oz milk | 12 oz milk |
| 6 | 39 | Cheese 1 oz | |
| 6 | 40 | Cheese 2 oz | |
| 6 | 41 | lactose tolerance achieved | |
| 6 | 42 | | |

The method of the present invention was initially tested on the applicant and after obtaining positive results, additional testing was performed on 10 adult human subjects. Five of the subjects followed the liquid protocol of Table 1, while the other five followed the capsule protocol of Table 2. Some of the test subjects experienced mild gas and discomfort at various points early in the program. At the end of the protocol, eight of the ten subjects tested considered themselves "cured" of lactose intolerance. One of the two who did not achieve the desired results interrupted the protocol by stopping in the middle and subsequently tried to restart a week later. This subject attributed his failure to stopping in the middle and to ingesting other foods such as creamed spinach, pizza, frozen yogurt, chocolate and other lactose containing foods during the protocol period. The other did not finish the six week protocol. The subjects who strictly followed the six-week protocol program for increasing lactose tolerance increased their lactose tolerance to a point where they are free to enjoy any lactose containing food of their choice.

Although the doses shown here have been used and tested, variations in the doses and timing in which they are administered can still result in an effective treatment for increasing tolerance for lactose containing products. For example, the presented doses have been tested on adult subjects. Thus, when applying the protocol of the present invention to younger subjects, the weight of the subject might be a consideration. For example, a subject weighing 50 pounds may not require, and may not be capable of tolerating, the doses set forth in Tables 1 and 2 at the prescribed time in the protocol. As such, the dose administered to the subject may be proportionally scaled down based on his weight. Although the two doses are disclosed as being administered with breakfast and dinner, alternatively the order of the doses maybe switched, or may be administered at other times of the day with meals such as lunch or snacks (or conceivably with no meals). Although the invention has been described for use in humans, it is also capable of being administered to other mammals.

The invention is not limited by the embodiments described above which are presented as examples only but can be modified in various ways within the scope of protection defined by the appended patent claims.

What is claimed is:

1. A method for increasing lactose tolerance in a subject experiencing lactose intolerance comprising the steps of:
 a) administering a first dosage of a lactose containing product to the subject each day for a first predetermined number of days,
 wherein said first predetermined number of days is 42 days, and
 wherein said first dosage comprises administering either about 1 tablespoon of milk or about 0.8 grams of lactose powder for days 1 to 3 of said first predetermined number of days;
 b) administering a pharmaceutically effective amount of live cultured bacteria to the subject each day in conjunction with the administration of said first dosage, the administration of the live cultured bacteria commencing on the first day of said first predetermined number of days and continuing for two days;
 c) increasing said first dosage over the course of said first predetermined number of days, said first dosage increasing at a rate of 1 additional tablespoon of milk or about 0.8 additional grams of lactose powder for each day beginning with day 4 of said first predetermined number of days such that by about day 18 of said first predetermined number of days said first dosage is about 16 tablespoons of milk or about 12.8 grams of lactose powder;
 d) administering a second dosage of the lactose containing product to the subject each day starting at day 19 of said first predetermined number of days, wherein said second dosage comprises about 1 tablespoon of milk or about 0.8 grams lactose powder; and
 e) increasing said second dosage over the course of said first predetermined number of days, wherein said second dosage increases at a rate of about 1 additional tablespoon of milk or about 0.8 additional grams of lactose powder for each day such that by about day 34 of said first predetermined number of days said second dosage is about 16 tablespoons of milk or about 12.8 grams of lactose powder, said second dosage being administered at a time of the day other than when said first dosage is administered.

2. The method set forth in claim 1, wherein said lactose powder is in capsule form.

3. The method set forth in claim 1, further comprising:
 f) discontinuing administration of the first and second dosages at day 35 of said first predetermined number of days; and
 g) administering to the subject a third dosage of a lactose containing product in a predetermined amount twice a day beginning at said day 35 and continuing for the remainder of said first predetermined number of days,
 wherein said third dosage comprises about 9 ounces of milk, said third dosage increasing at a rate of 1 ounce of milk each day for three days such that on about day 38 of said first predetermined number of days said third dosage comprises about 12 ounces of milk.

4. The method set forth in claim 3, further comprising discontinuing the administration of said third dosage on about day 39 of said first predetermined number of days and administering about 1 or 2 ounces of cheese for two days thereafter with dinner.

5. The method set forth in claim 3, wherein the dosages of the lactose containing products are administered without meals.

6. The method set forth in claim 3, wherein the dosages of the lactose containing products are administered in conjunction with meals.

7. The method set forth in claim 6, wherein the administration of said first dosage is performed with dinner, the administration of said second dosage is performed with breakfast, and the administration of said third dosage is performed with both breakfast and dinner.

* * * * *